United States Patent [19]

Iwatschenko

[11] 4,306,563

[45] Dec. 22, 1981

[54] CATHETER FOR INTRODUCTION INTO BODY CAVITIES

[75] Inventor: Peter Iwatschenko, Neunkirchen, Fed. Rep. of Germany

[73] Assignee: Firma Pfrimmer & Co. Pharmazeutische Werke Erlangen GmbH, Erlangen, Fed. Rep. of Germany

[21] Appl. No.: 98,164

[22] Filed: Nov. 28, 1979

Related U.S. Application Data

[62] Continuation-In-Part of Serial No. 06/067,495, Filed Aug. 16, 1979, Now Abandoned.

[51] Int. Cl.³ .............................................. A61M 25/00
[52] U.S. Cl. ................................. 128/349 R; 128/348
[58] Field of Search ............. 128/348, 349, 127, 260, 128/130, DIG. 8; 3/1

[56] References Cited

U.S. PATENT DOCUMENTS

| | | | |
|---|---|---|---|
| 2,956,884 | 10/1960 | Caldwell | 96/114 |
| 3,106,483 | 8/1963 | Kline | 128/348 |
| 3,695,921 | 10/1972 | Shepherd et al. | 128/348 |
| 3,700,609 | 10/1972 | Tregear et al. | 260/2.5 R |
| 3,800,792 | 4/1974 | McKnight et al. | 128/156 |
| 3,808,113 | 4/1974 | Okamura et al. | 128/214 D |
| 3,939,049 | 2/1976 | Ratner et al. | 204/159.13 |
| 3,941,858 | 3/1976 | Shepherd et al. | 3/1 |
| 3,975,350 | 8/1976 | Hudgin et al. | 128/127 |
| 4,060,081 | 11/1977 | Yannas et al. | 128/156 |

Primary Examiner—Robert W. Michell
Assistant Examiner—T. J. Wallen
Attorney, Agent, or Firm—Jordan and Hamburg

[57] ABSTRACT

A catheter for the introduction into body cavities is made out of high-molecular material such as plastic, latex or the like and a physiologically compatible external stiffening coating thereon, the stiffening coating comprising a material soluble in body fluids.

9 Claims, 1 Drawing Figure

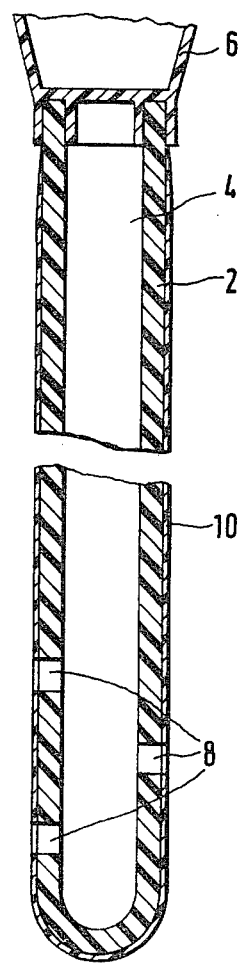

CATHETER FOR INTRODUCTION INTO BODY CAVITIES

BACKGROUND OF THE INVENTION

This Application is a Continuation-In-Part of Serial No. 06/067,495, Filed Aug. 16, 1979, Now abandoned.

This invention relates to a catheter for introduction into body cavities which is made out of a high molecular material, for example plastic or latex, and a physiologically compatible external rigidizing coating. The word catheter as used herein is to be understood in its general meaning and embraces, for example catheters, vein-catheters and similar products.

Two different and by themselves contradictory demands are important for such catheters. On the one hand they must be sufficiently stiff for the introduction into the body cavity in order to have such procedure easily effected. That is particularly important when the patient is not capable to aid the introduction by swallowing motions or also when the introduction must be handled against reflex motions of the body. On the other hand the catheter must be soft and flexible when introduced, because it must dwell within the patient for extended periods on some occasions and should not incommode or prevent the patient from moving freely. When such catheters remain several days in the stomach or in the duodenum or in other body cavities, they should not become hard due to the loss of softeners, because that would lead to pressure necroses.

Known soft-vinyl catheters presently used do not fulfil the last mentioned requirement. Such PVC-catheters are cooled prior to introduction (see, for instance German DE-AS 21 40 994) in order to increase temporarily their rigidity. On the other hand catheters made out of highly elastic materials are known, for example made from silicone rubber or latex, which are tolerated by patients with relative ease for even long dwelling times. For these catheters, however, the introduction is rather problematical. Therefore, a rigidizing element is provided or introduced in the catheter, a wire for instance, which is removed from the catheter once it is introduced into the body cavity sufficiently. It is disadvantageous, however, that the introduction of the wire necessitates painstaking manipulations and furthermore, the danger exists that the wire might puncture the thin catheter wall and that internal injuries of the patient might result. Furthermore, the aforementioned German DE-AS 21 40 994 also discloses that the catheter itself be provided with a coating of silicone resin or fluorocarbon resin but which serves mainly to increase the compatibility with the body and to prevent eventual toxic reactions.

SUMMARY OF THE INVENTION

Accordingly, it is the objective of the present invention to provide a catheter which has the rigidity sufficient to perform this process free of difficulties and which is on the other hand so soft while dwelling in the body of the patient that the patient is able to bear it without complaints, and which finally may be manufactured at a reasonable cost and which allows the introduction into the body cavity without painstaking preparations.

Other features which are considered characteristic of the invention are set forth in the appended claims.

Although the invention is illustrated and described in relationship to specific embodiments, it is nevertheless not intended to be limited to the details shown, since various modifications and structural changes may be made therein without departing from the spirit of the invention and within the scope and range of equivalents of the claims.

The construction and operation of the invention, however, together with additional objects and advantages thereof will be best understood from the following description of specific embodiments when read in connection with the accompanying drawings.

BRIEF DESCRIPTION OF THE DRAWING

The accompanying FIGURE shows the catheter in cross section.

DESCRIPTION OF THE PREFERRED EMBODIMENTS

The objective of the present invention is attained for a catheter of the aforementioned kind by using for the rigidizing coating a material that is soluble in the liquids of the body. In the simplest case such a coating may be soluble in water. It is within the scope of the present invention also, to provide for special uses a coating which is, for example, soluble in a slightly basic medium (sputum) or in a slightly acid medium (gastric juice). A rigidizing coating of this kind, for which various physiologically innocuous and also economically advantageous materials may be considered, makes it possible to introduce the catheter into the patient without any preparatory actions. The thickness and material of the coating may be chosen, so that when introducing the catheter the optimal rigidity may be chosen, independent from any parameters characterizing the present use, such as for instance, the temperature. The rigidizing coating dissolves in the body fluids existing in which ever body cavity it is introduced, within more or less time and what remains is only the highly flexible catheter so that the patient may bear it without difficulties and for prolonged periods of time.

It is particularly advantageous to use gelatine as the coating stiffening material. Gelatine is an inexpensive material easily worked with and soluble in water, therefore soluble in practically all body fluids within reasonable times. Furthermore, gelatine has a netural taste so that catheters coated therewith are not objectionable when orally introduced. A catheter made out of silicone rubber or latex for instance, may be coated in a gelatine bath, preferably with a thickness of from 0.05 mm to 0.2 mm.

It is particularly advantageous to add to the gelatine a certain amount of a physiologically compatible polyvalent alcohol as a softener. In this manner the hardness of the gelatine coating may be determined beforehand. Under certain circumstances the initial stiffness of pure gelatine coatings may be reduced slightly so that the catheter is on one hand sufficiently rigid for safe introduction but may be on the other hand also flexible enough in order to follow the curvatures of the body cavities. Mainly, though, breaking danger is greatly diminished for the gelatine coating. That may be attained, for instance, by adding from 0.5 to 10% by weight glycerol, preferably 0.5 to 5% based on the weight of the gelatine.

Furthermore it may be advantageous to provide the gelatine with a portion of formaldehyde or another aldehyde. That is particularly advantageous when the introductory process takes a longer time so that the stiffening coating of the catheter dissolves in the body fluids before reaching its final position, which would therefore prevent the introduction or make it very difficult. Aldehydes make the gelatine hydrophobic or soluble in which case the degree of tanning regulates the time of solution. An addition of, for instance, from 0.1 to 2% by weight of formaldehyde based on the weight of the gelatine makes the gelatine sufficiently hydrophobic or soluble.

In another advantageous embodiment of the present invention the stiffening coating may consist of polyvinyl alcohol, preferably with a portion of 10–25% acetate groups ($CH_3$—COO). The thickness of the stiffening coating should be in this case between about 0.05 and 0.1 mm. This ensures sufficient time between the introduction of the catheter and the solution of the PVA-film. Rigidity and water solubility are influenced by the type of PVA used, where particularly those with 10 to 25% acetate are particularly advantageous.

Catheters furnished with a stiffening coating may be prepared, sterilized and packaged as usual.

The accompanying drawing illustrates one embodiment of the present invention and shows a catheter or tubing 2 having a hollow passage 4 and mounted on an adapter 6. Holes 8 are provided in the catheter for substance to pass into the catheter and stiffening coating 10 is provided over the outside of the catheter 2.

It is thought that the invention and many of its attendant advantages will be understood from the foregoing description and that it will be apparent that various changes may be made in the form, construction, and arrangements of the parts without departing from the spirit and scope of the invention or sacrificing all of its material advantages. The form heretofore described being merely a preferred embodiment thereof.

What is claimed is:

1. A catheter for temporary introduction into body cavities and adapted for one-time use, said catheter being made of a soft, highly flexible, and high-molecular material such as plastic, latex, or the like and a physiologically compatible external stiffening coating of gelatine thereon to provide temporary sufficient stiffness to the catheter in order to facilitate insertion of the catheter into a body cavity, said gelatine coating being soluble in body fluids, said gelatine coating providing sufficient stiffness to the catheter to enable the catheter to be readily inserted in a body cavity, said gelatine coating dissolving in said cavity to thereby expose said soft, high-flexible, and high-molecular material to thereby provide indwelling comfort over extended periods of time until withdrawn.

2. A catheter according to claim 1 wherein said stiffening coating further comprises a physiologically compatible polyvalent alcohol as a softener.

3. A catheter according to claim 2 wherein said polyvalent alcohol is glycerol in the proportion of from 0.5 to 5% by weight, based on the weight of the stiffening coating.

4. A catheter according to claim 2 wherein said polyvalent alcohol is glycerol in the proportion of from 0.5 to 10% by weight, based on the weight of the stiffening coating.

5. A catheter according to claim 1 wherein said stiffening coating further comprises an aldehyde.

6. A catheter according to claim 5 wherein said aldehyde is formaldehyde.

7. A catheter according to claim 5 wherein the proportion of said aldehyde is form 0.1 to 2% by weight, based on the weight of the gelatine.

8. A catheter according to claim 1 wherein said stiffening coating has a thickness of from 0.05 mm to 0.2 mm.

9. The method of rigidizing a catheter of the type which is temporarily used one time to facilitate insertion into a body cavity and removing said rigidity after insertion to provide indwelling comfort for extended periods of time until withdrawn from the body cavity, comprising coating a soft, highly flexible, and high-molecular material such as plastic, latex or the like with a physiologically compatible external stiffening coating of gelatine, and causing said gelatine coating to be dissolved by the body fluids to thereby expose said soft, highly flexible, highly-molecular material to provide indwelling comfort over extended periods of time until withdrawn.

* * * * *